United States Patent
Coppola et al.

(10) Patent No.: US 8,575,412 B2
(45) Date of Patent: Nov. 5, 2013

(54) PROCESSES FOR PREPARING TRIPHENYLENE

(75) Inventors: Kevin Coppola, Baton Rouge, LA (US); Christopher D. Claeboe, Hamilton, MI (US); Bruce C. Berris, Baton Rouge, LA (US)

(73) Assignee: Albemarle Corporation, Baton Rouge, LA (US)

( * ) Notice: Subject to any disclaimer, the term of this patent is extended or adjusted under 35 U.S.C. 154(b) by 198 days.

(21) Appl. No.: 13/131,773

(22) PCT Filed: Oct. 28, 2009

(86) PCT No.: PCT/US2009/062352
§ 371 (c)(1),
(2), (4) Date: May 27, 2011

(87) PCT Pub. No.: WO2010/065216
PCT Pub. Date: Jun. 10, 2010

(65) Prior Publication Data
US 2011/0301395 A1  Dec. 8, 2011

Related U.S. Application Data

(60) Provisional application No. 61/117,743, filed on Nov. 25, 2008.

(51) Int. Cl.
*C07C 5/367* (2006.01)

(52) U.S. Cl.
USPC ........... 585/431; 585/400; 585/430; 585/434; 585/812; 585/815; 585/817

(58) Field of Classification Search
USPC .......... 585/400, 430, 431, 434, 812, 815, 817
See application file for complete search history.

(56) References Cited

U.S. PATENT DOCUMENTS

| | | | | |
|---|---|---|---|---|
| 3,325,551 | A | * | 6/1967 | Suld .............................. 585/411 |
| 3,387,051 | A | * | 6/1968 | Norell ........................... 585/431 |
| 4,999,326 | A | * | 3/1991 | Sikkenga et al. ............... 502/30 |
| 7,351,395 | B1 | | 4/2008 | Pez et al. |

FOREIGN PATENT DOCUMENTS

WO  WO 90/15776  12/1990

OTHER PUBLICATIONS

Resasco, "Dehydrogenation—Heterogeneous" in Encyclopedia of Catalysis, John Wiley & Sons, 2002, available on-line Jul. 15, 2002.*
n-Paraffin Boiling Points in Lange's Handbook of Chemistry, J. G. Speight, ed., McGraw-Hill, 2005, available on-line Apr. 19, 2007 at www.knovel.com.*
"Triphenylene" in The Merck Index, Merck & Co., M. J. O'Neil, ed., available on-line at www.knovel.com on Dec. 1, 2007.*
"Commercial Hydrocarbon Solvents" in Significance of Tests for Petroleum Products, 8th ed., ASTM International, 2010, S. J. Rand, ed., available on-line at www.knovel.com on Jan. 5, 2011.*
L.H. Klemm, et al: "Chemical Structure and Chromatographic Adsorbability of Aromatic Hydrocarbons on Alumina"; The Journal of Organic Chemistry, vol. 24, No. 10; Oct. 1959; pp. 1468-1477.
Homer Adkins, et al: "Catalytic Dehydrogenation of Hydroaromatic Compounds with Benezene"; Journal of the American Chemical Society, vol. 63, No. 5; May 1941; pp. 1320-1325.
C.C. Barker, et al: "214. Triphenylene: An Examination of Modified Mannich Syntheses, and an Improvement of the Rapson Synthesis"; Journal of the Chemical Society; 1958; pp. 1077-1080.
L.H. Klemm, et al: "The Insertion and Extrusion of Heterosulfur Bridges. XIV. Synthesis of Nitrotriphenyleno[1,12-bcd]thiophenes [1]"; Journal of Heterocyclic Chemicals, vol. 34; 1967; pp. 1749-1757.

* cited by examiner

*Primary Examiner* — In Suk Bullock
*Assistant Examiner* — Bradley Etherton
(74) *Attorney, Agent, or Firm* — Marcy M. Hoefling; James A. Jubinsky; Nathan C. Dunn

(57) ABSTRACT

Processes are provided for producing triphenylene by combining at least dodecahydrotriphenylene, a dehydrogenation catalyst such as palladium on carbon, and an aliphatic solvent having a boiling point greater than 180° C. to form a reaction mixture, heating the reaction mixture to at least about 180° C. but lower than the boiling point of the aliphatic solvent, maintaining the temperature of the reaction mixture at 180° C. but lower than the boiling point of the aliphatic solvent, and passing a purge fluid comprising an inert fluid through the reaction mixture, for a period of time adequate for production of triphenylene.

7 Claims, No Drawings

PROCESSES FOR PREPARING TRIPHENYLENE

BACKGROUND

Triphenylene is useful in manufacturing optical and electronic devices. It can be prepared by the catalytic dehydrogenation of dodecahydrotriphenylene. However, currently known dehydrogenation processes/reactions are slow and reversible. In addition, it is exceedingly difficult to separate the triphenylene product from the dehydrogenation catalyst.

Thus, there is a need for improved processes for preparing triphenylene. Particularly such processes that would be suitable for commercial use.

THE INVENTION

This invention meets the above-described needs by providing processes comprising: (a) combining at least dodecahydrotriphenylene, a dehydrogenation catalyst, and an aliphatic solvent having a boiling point greater than 180° C. to form a reaction mixture, (b) heating the reaction mixture to at least about 180° C. but lower than the boiling point of the aliphatic solvent, (c) maintaining the reaction mixture between at least about 180° C. and the boiling point of the aliphatic solvent, and passing a purge fluid comprising an inert fluid through the reaction mixture, for a period of time adequate for producing triphenylene, e.g., for at least about 12 hours, and (d) producing triphenylene. In processes of this invention, producing triphenylene can comprise: (a) cooling the reaction mixture, e.g., to about 130° C.; (b) combining at least the cooled reaction mixture and a halogenated co-solvent to form a filtration mixture; (c) heating the filtration mixture to at least about 125° C.; (d) filtering the filtration mixture to recover a filtrate; (e) cooling the filtrate to ambient; and (f) collecting triphenylene from the filtrate.

Processes according to this invention can be illustrated with the following reaction scheme:

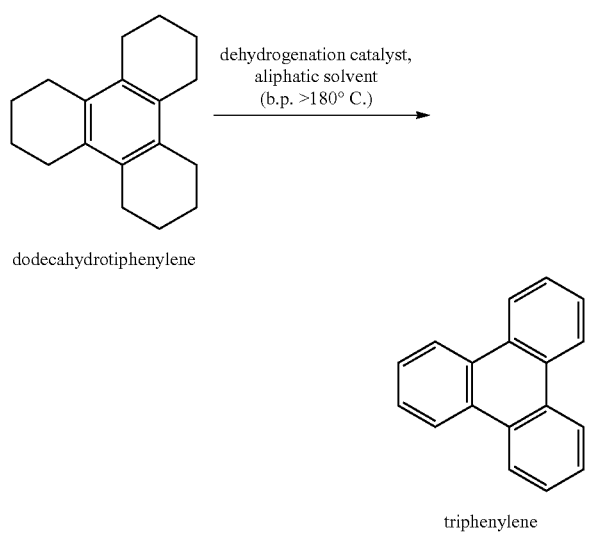

In processes according to this invention, use of a de-aromatized and de-olefinized solvent having a high boiling point, e.g., of greater than about 180° C., or even greater than about 220° C., can greatly accelerate formation of triphenylene. Thus the reaction can be conducted at temperatures up to about 438° C., e.g., from about 180° C. to about 260° C., and at these higher temperatures the reaction proceeds much more quickly, than in prior processes for producing triphenylene. The reaction can be complete in from 24 to 48 hours. Completion can be determined by analyzing the reaction mixture to detect the desired production of triphenylene, e.g., by gas chromatography measurements. The chemistry is also driven by applying an inert purge to the system to drive the reaction. This inert purge removes hydrogen from the system which drives the reaction equilibrium. The catalyst is easily recovered from the system by addition of halogenated solvent and removing catalyst by hot filtration. The triphenylene product can then be precipitated from the solvent mixture upon cooling. Catalyst recovered this way can easily be recycled into the next batch.

Dehydrogenation Catalyst

Dehydrogenation catalysts suitable for use in processes of this invention can comprise palladium on carbon, platinum, and/or nickel. For example, 5% Pd/C (50% wet) is a suitable dehydrogenation catalyst.

Aliphatic Solvent

Aliphatic solvents suitable for use in processes of this invention have a boiling point greater than 180° C. Suitable aliphatic solvents comprise those having substantially no aromatics, e.g., less than about 1.5% aromatics, and substantially no olefins, e.g., less than about 1.5% olefins. Aliphatic solvents useful in processes of this invention can comprise tetradecane or pentadecane. Additionally, some petroleum hydrotreated light distillate products sold by ExxonMobil in its EXXSOL product line boil in the range of about 220° C. to about 260° C., e.g., CAS number 64742-47-8, and are suitable for use in processes of this invention. The EXXSOL family of solvents comprise mixtures of de-olefinized and de-aromatized higher aliphatics. Exxsol 95 boils in the 224-238° C. range while Exxsol 110 boils in the 249-268° C. range.

Halogenated Co-Solvent

Halogenated co-solvents suitable for use in processes of this invention have boiling points in the range of 50° C. to 200° C., e.g., 50° C. to 150° C., or 100° C. to 200° C., and can comprise dichloroethane, chloroform, methylene chloride or chlorobenzene.

If desired, the halogenated co-solvent may be concentrated and the resultant solid may then be filtered, dried, and recycled to increase process efficiency. Recovered co-solvent may also be recycled.

Purge Fluid

A purge fluid, such as nitrogen gas, is passed through the reaction mixture while the temperature of the reaction mixture is maintained above about 180° C. Additionally, a purge fluid can be passed through the reaction mixture as the reaction mixture is heated to at least about 180° C. Purge fluids suitable for use in processes of this invention comprise inert fluids such as nitrogen, carbon dioxide, and the like, and include such fluid in the gaseous form.

Given the teachings of this disclosure, one skilled in the art can determine the desired purge rate. A primary consideration in determining the purge rate is the volume of the reaction mixture and/or container in which the reaction mixture is contained. For example, a suitable purge rate for a reaction mixture in a 1 liter container is at least about 1 liter/hour of purge fluid.

An advantage of this invention is that the two solvent system is easily separated by distillation, capitalizing on the wide difference in boiling points, and both solvents may readily be recycled. Recovered yield will depend a great deal upon the quantity of halogenated co-solvent used i.e. too much will lower the recovered yield. However, an insufficient quantity of halogenated co-solvent will facilitate rapid product crystallization.

EXAMPLES

The following examples are illustrative of the principles of this invention. It is understood that this invention is not limited to any one specific embodiment exemplified herein, whether in the examples or the remainder of this patent application.

Example 1

1. A 12-L, 4-necked reaction flask bearing an outlet valve at its base, was fitted with a mechanical stirring apparatus, high-efficiency condenser with a gas outlet, a thermocouple, and an $N_2$-inlet.
2. The system was charged with 1.5 kg (6.24 mol) of dodecahydrotriphenylene, 2.0 L of EXXSOL 110 fluid (CAS number 64742-47-8), and 125 g of 5% Pd/C (50 wt. % water).
3. The mixture was stirred and heated using a split-heating mantle to 110° C. for 6 h to remove excess water as steam through the uncooled reaction condenser with an $N_2$-sweep.
4. Water was applied to the condenser as a coolant, then the reaction mixture was heated to 225° C. and held at 225° C. for an additional 40 h while maintaining a slight $N_2$-sweep.
5. Upon completion, the reaction mixture was cooled slowly to 130° C. and then 5.0 L of chlorobenzene was added.
6. The mixture was reheated to 125° C. and rapidly filtered through a jacketed, glass-fritted funnel containing a pad of celite that was heated to 105° C. using either a heated fluid.
7. The filtrate was cooled to ambient temperature over 12 h, the product triphenylene crystallized.
8. The triphenylene solid was collected by filtration and then washed with 4.0 kg of acetone.
9. The triphenylene solid was then dried under vacuum at 50° C. for 12 h to afford about 1.0 kg (4.38 mol) of the target compound in a yield of 70%.

The mass balance for Example 1 follows:

| component | CAS # | FW (g $mol^{-1}$) | mass (kg) | mol | bp/mp (° C.) |
|---|---|---|---|---|---|
| dodecahydrotri-phenylene | 1610-39-5 | 240.38 | 1.50 | 6.24 | |
| EXXSOL D110 | | | 2.0 | | 249-268/— |
| 5% Pd/C (50% wet) | | | 0.125 | | |
| chlorobenzene | 108-90-7 | 112.56 | 5.5 | | 132/−45 |
| acetone | 67-64-1 | 58.08 | 4.0 | | 56/−94 |
| triphenylene | 217-59-4 | 228.29 | 1.00 | 4.38 | 438/196 |
| Waste | | | | | |
| acetone + EXXSOL | | | 6.0 | | |
| celite + catalyst | | | 0.250 | | |
| chlorobenzene | | | recycled | | |

Example 2

To a 3-necked, 5-L round bottom flask that is fitted with a mechanical stirring apparatus, thermometer and a condenser is added 630 g (2.62 mol) of 1,2,3,4,5,6,7,8,9,10,11,12-dodecahydrotriphenylene, 1.0 L of Exxsol D110 fluid (CAS number 64742-47-8), and 14.5 g of 5% Pd/C (50% wet). The mixture is heated to 110° C. for 4 hours to facilitate the gentle evolution of water from the catalyst as steam. Then the mixture is heated to 225° C. with stirring for 48 hours. Then the reaction mixture is cooled to 130° C. and diluted with 1.5 L of chlorobenzene. Once the pot temperature is re-heated to 120° C., the mixture is passed over celite in a steam-jacketed frit under vacuum. Upon cooling to ambient temperature over 6 hours, the crystalline product is collected by filtration and washed with 1.0 kg of acetone. The triphenylene product is dried under vacuum at 50° C. for 12 hours to afford 406 g (1.78 mol) of the desired product in a yield of 68%.

It is to be understood that the reactants and components referred to by chemical name or formula anywhere in the specification or claims hereof, whether referred to in the singular or plural, are identified as they exist prior to being combined with or coming into contact with another substance referred to by chemical name or chemical type (e.g., another reactant, a solvent, or etc.). It matters not what chemical changes, transformations and/or reactions, if any, take place in the resulting combination or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a combination to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, combined, blended or mixed with one or more other substances, components and/or ingredients in accordance with the present disclosure. Whatever transformations, if any, which occur in situ as a reaction is conducted is what the claim is intended to cover. Thus the fact that a substance, component or ingredient may have lost its original identity through a chemical reaction or transformation during the course of contacting, combining, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof. As will be familiar to those skilled in the art, the terms "combined", "combining", and the like as used herein mean that the components that are "combined" or that one is "combining" are put into a container with each other. Likewise a "combination" of components means the components having been put together in a container.

While the present invention has been described in terms of one or more preferred embodiments, it is to be understood that other modifications may be made without departing from the scope of the invention, which is set forth in the claims below.

What is claimed is:
1. A process comprising:
  (a) combining at least dodecahydrotriphenylene, a dehydrogenation catalyst, and an aliphatic solvent having a boiling point greater than 180° C. to form a reaction mixture,
  (b) heating the reaction mixture to at least about 180° C. but lower than the boiling point of the aliphatic solvent,
  (c) maintaining the reaction mixture between at least about 180° C. and the boiling point of the aliphatic solvent, and passing a purge fluid comprising an inert fluid through the reaction mixture, for at least about 12 hours,
  (d) adding a halogenated co-solvent to the reaction mixture; and
  (e) producing triphenylene.

2. The process according to claim 1 wherein the dehydrogenation catalyst comprises palladium on carbon or platinum.

3. The process according to claim 1 wherein the aliphatic solvent comprises tetradecane or pentadecane.

4. The process according to claim 1 wherein (d) is replaced with:
(d) cooling the reaction mixture;
(e) combining at least the cooled reaction mixture and a halogenated co-solvent to form a filtration mixture;
(f) heating the filtration mixture to at least about 125° C.;
(g) filtering the filtration mixture to recover a filtrate;
(h) cooling the filtrate to ambient; and
(i) collecting triphenylene from the filtrate.

5. The process according to claim 1, further comprising passing a purge fluid through the reaction mixture during (b).

6. The process according to claim 1 wherein the halogenated co-solvent comprises dichloroethane, chloroform, methylene chloride, or chlorobenzene.

7. A process comprising:
(a) combining at least dodecahydrotriphenylene, palladium on carbon, and an aliphatic solvent comprising tetradecane or pentadecane and having a boiling point greater than 180° C. to form a reaction mixture,
(b) heating the reaction mixture to at least about 180° C. but lower than the boiling point of the aliphatic solvent,
(c) maintaining the reaction mixture between at least about 180° C. and the boiling point of the aliphatic solvent, and passing a purge fluid comprising an inert fluid through the reaction mixture, for at least about 12 hours,
(d) adding a halogenated co-solvent to the reaction mixture; and
(e) producing triphenylene.

* * * * *

UNITED STATES PATENT AND TRADEMARK OFFICE
CERTIFICATE OF CORRECTION

PATENT NO. : 8,575,412 B2  Page 1 of 1
APPLICATION NO. : 13/131773
DATED : November 5, 2013
INVENTOR(S) : Coppola et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 200 days.

Signed and Sealed this
Twenty-second Day of September, 2015

Michelle K. Lee
*Director of the United States Patent and Trademark Office*